(12) United States Patent
Vija et al.

(10) Patent No.: US 7,569,809 B2
(45) Date of Patent: Aug. 4, 2009

(54) FLOW-DRIVE FOR DYNAMIC PHANTOM

(75) Inventors: A. Hans Vija, Evanston, IL (US); Johannes Zeintl, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 287 days.

(21) Appl. No.: 11/524,824

(22) Filed: Sep. 21, 2006

(65) Prior Publication Data

US 2008/0078235 A1    Apr. 3, 2008

(51) Int. Cl.
*G01D 18/00* (2006.01)
(52) U.S. Cl. ............ 250/252.1; 600/436; 700/282
(58) Field of Classification Search ......... 250/252.1
See application file for complete search history.

(56) References Cited

U.S. PATENT DOCUMENTS

| | | | |
|---|---|---|---|
| 5,052,934 A * | 10/1991 | Carey et al. ............. 434/268 |
| 6,148,655 A * | 11/2000 | Hall et al. ............... 73/1.83 |
| 6,318,146 B1 * | 11/2001 | Madsen et al. .......... 73/1.86 |
| 6,526,308 B1 * | 2/2003 | Heikkinen ............... 600/436 |
| 6,744,039 B1 * | 6/2004 | DiFilippo ................ 250/252.1 |
| 2003/0045803 A1 * | 3/2003 | Acharya .................. 600/508 |
| 2003/0220718 A1 * | 11/2003 | Jaszczak et al. ......... 700/282 |

* cited by examiner

*Primary Examiner*—David P Porta
*Assistant Examiner*—Jessica L Eley

(57) ABSTRACT

Apparatus and method for simulating tracer interaction with living tissue. A chamber receives a fluid therein, and includes an inlet conduit for conducting the fluid into the chamber, an outlet conduit for conducting the fluid out of the chamber, a medium disposed within the chamber for modulating fluid flow, and a valve assembly for conducting the fluid into the inlet conduit. In some aspects, the fluid is a radiative tracer or a radiative washout fluid and the medium is configured to mimic a tissue, e.g., the heart, and portions thereof are capable of mimicking both normal and diseased tissues.

27 Claims, 7 Drawing Sheets

FIG. 1

PRIOR ART

FLOW-DRIVE FOR DYNAMIC PHANTOM

FIELD OF THE INVENTION

The present invention relates generally to nuclear imaging devices, and more particularly, to phantoms for use therewith for purposes of simulating anatomical conditions.

BACKGROUND OF THE INVENTION

Nuclear medicine is a unique medical specialty wherein radiation is used to acquire images which show the function and anatomy of organs, bones or tissues of the body. Generally, low-level radiopharmaceuticals are ingested or injected into the body and carried to the specific organs, bones or tissues. Gamma photon emitted by the radiopharmaceuticals are then captured by a gamma camera of the imaging device and used to prepare images of the target. In this way, specific organs, bones or tissues and/or functions thereof can be studied with minimal impact upon the patient or subject being studied.

In order to prepare images, however, it is necessary to calibrate and ensure the accuracy and proper working order of the nuclear imaging device to be used. This is commonly performed by the use of calibration instruments, known as phantoms. Generally, phantoms are structures having known parameters, which can include, but are not limited to, specific dimensions and/or radiation levels. Accordingly, an image of a phantom produced by a nuclear imaging device can be compared with the actual phantom to determine, for example, image quality, background radiation levels, attenuation information, etc.

In addition to their use as calibration devices, phantoms can also be used for other purposes such as, for example, simulating anatomical conditions for purposes of training individuals to properly use a medical imaging device and/or for training individuals how to read images and/or render diagnoses from the images produced by a medical imaging device. Accordingly, there are various types of phantom and the particular phantom to be used in a simulation depends on a number of factors, which include but are not limited to: specific anatomical area to be studied, e.g., heart, lungs, etc., specific anatomical condition/anomaly to be studied, e.g., normal vs. diseased tissue, etc., and environment, e.g., calibration vs. training. Indeed, phantoms currently range from mere computer software programs, to simple cylindrical devices primarily used for calibration purposes, to more complex mechanical devices that can include pumping mechanisms for mimicking moving body parts, e.g., the human heart.

While there are known several types of phantom for simulating anatomical conditions, one mechanical-type is described in U.S. Pat. App. Pub. No. 2003/0220718 A1, which published application is incorporated herein by reference in its entirety. The phantom disclosed in that application generally relates to a dynamic cardiac phantom for simulating the beating of a human heart and includes inner and outer elastomeric members defining a void therebetween; the void is intended to mimic the myocardium of the human heart and is capable of being filled with a radiative tracer. The dynamic cardiac phantom, thus, can be used to simulate and image the systolic and diastolic functions of the human heart. Another dynamic cardiac phantom is disclosed in U.S. Pat. App. Pub. No. 2003/0045803 A1 which published application is also incorporated herein by reference in its entirety.

While the dynamic cardiac phantoms described in U.S. Pat. App. Pub. Nos. 2003/0220718 A1 and 2003/0045803 A1 may be useful for accomplishing their intended purposes, it is also desirable to simulate other anatomical functions and/or characteristics of organs, tissues or bones. For example, because diseased or abnormal tissue can tend to more rapidly "wash-in" or more rapidly "wash-out" certain tracers when compared with normal, non-diseased tissue, it can be desirable to monitor tracer wash-in and wash-out for diagnostic purposes. Accordingly, it is also desirable to simulate wash-in and wash-out.

What is needed then is a phantom that is capable of simulating tracer wash-in and washout, e.g., radiative tracer, uptake, residence, and/or processing by organs, tissues or bones.

SUMMARY OF THE INVENTION

An apparatus for simulating tracer interaction with a tissue generally comprises a chamber for receiving a fluid therein, an inlet conduit for conducting the fluid into the chamber, an outlet conduit for conducting the fluid out of the chamber, a medium disposed within the chamber for modulating fluid flow, and a valve assembly for conducting the fluid into the inlet conduit. In some aspects, the fluid is a radiative tracer or a radiative washout fluid and the medium is configured to mimic a tissue, e.g., the heart, and portions thereof are capable of mimicking both normal and diseased tissues.

In some aspects the medium comprises an aggregate-type material and has an attenuation characteristic similar to that of water. In some aspects, the medium comprises Lucite, which can be granular or beaded form. In some aspects, the chamber includes a distribution assembly for uniformly distributing fluid into the chamber. In some aspects, the chamber includes an inner chamber wall and an outer chamber wall, and the inner chamber wall and the outer chamber wall are disposed relative to one another to thereby form a chamber conduit therebetween.

In some aspects the chamber conduit fluidly connects to the inlet conduit and the outlet conduit, the inner chamber wall includes a plurality of apertures for conducting the fluid to the medium, and the medium is disposed in the chamber conduit. In other aspects, the medium is disposed inward of said inner chamber wall. In some aspects, chamber comprises an expandable chamber wall, for example, for mimicking organs such as the human heart.

A method for simulating radiative tracer interaction with a tissue generally comprises issuing a first fluid into a chamber comprising a medium via of a valve connected to an input conduit, bathing the medium with the first fluid and allowing the first fluid to exit the chamber via an outlet conduit, monitoring the chamber with a medical imaging device, e.g. to monitor the uptake of a radiative tracer by the medium, issuing a second fluid, e.g. a radiative wash, into the chamber via the input conduit, bathing the medium with the second fluid and allowing the second fluid to exit the chamber, and monitoring the chamber with the medical imaging device, e.g. to monitor egress of the radiative tracer from the medium.

In some aspects of the method, the medium has an attenuation characteristic substantially similar to water and/or comprises an aggregate-type material, which can be beads, or Lucite beads. In some aspects of the method, the medium is disposed within the chamber, which can comprise inner and outer chamber walls thereby forming a chamber conduit. In some aspects of the method, the medium is disposed within the chamber conduit, which can be fluidly connected to the inlet an inlet and outlet conduit of the chamber. In some aspects of the method, the chamber can comprise an expandable chamber wall.

These and other aspects, features and advantages of the present invention will become readily apparent to those having ordinary skill in the art upon a reading of the following detailed description of the invention in view of the drawings.

BRIEF DESCRIPTION OF THE DRAWINGS

The invention will now be more fully described by way of example with reference to the accompanying drawings in which.

DETAILED DESCRIPTION OF THE INVENTION

The present invention will now be described and disclosed in further detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention. Also, it should be appreciated that, in the detailed description of the invention that follows, like reference numbers on different drawing views are intended to identify like structural elements, and/or functionally equivalent elements, of the invention in the respective views.

Figure 1:
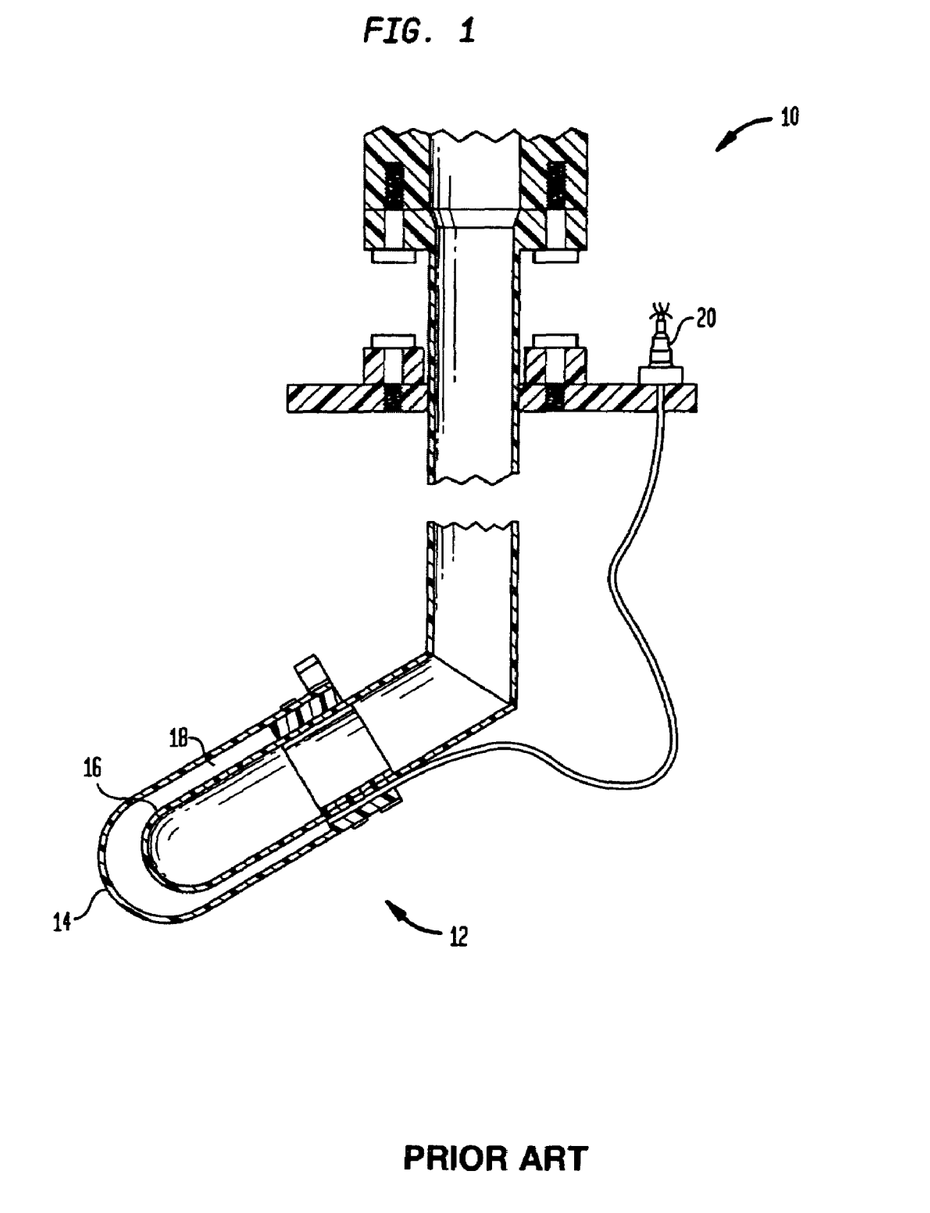
FIG. 1 is a perspective view of a known dynamic cardiac phantom.

Referring now to FIG. 1, which is a view of a known dynamic cardiac phantom as described in U.S. Pat. App. Pub. No. 2003/0220718 A1, known dynamic cardiac phantom 10 includes elastomeric heart portion 12 formed from a first, outer elastomeric sleeve 14 and a second, inner elastomeric sleeve 16. First outer elastomeric sleeve 14 and second inner elastomeric sleeve 16 are separated from one another by void 18, which is intended to simulate the myocardium of the human heart. Valve assembly 20 is provided for introducing a radiative fluid into void 18 such that the simulated myocardium can be imaged using a nuclear imaging device when the phantom is operated, for example, contracted and/or expanded to simulate systolic and diastolic functions of a human heart. As may be appreciated from FIG. 1, dynamic cardiac phantom 10 is not configured for first introducing a flow in and out of the myocardial void so as to simulate/monitor tracer wash-in and wash-out.

Figure 2:
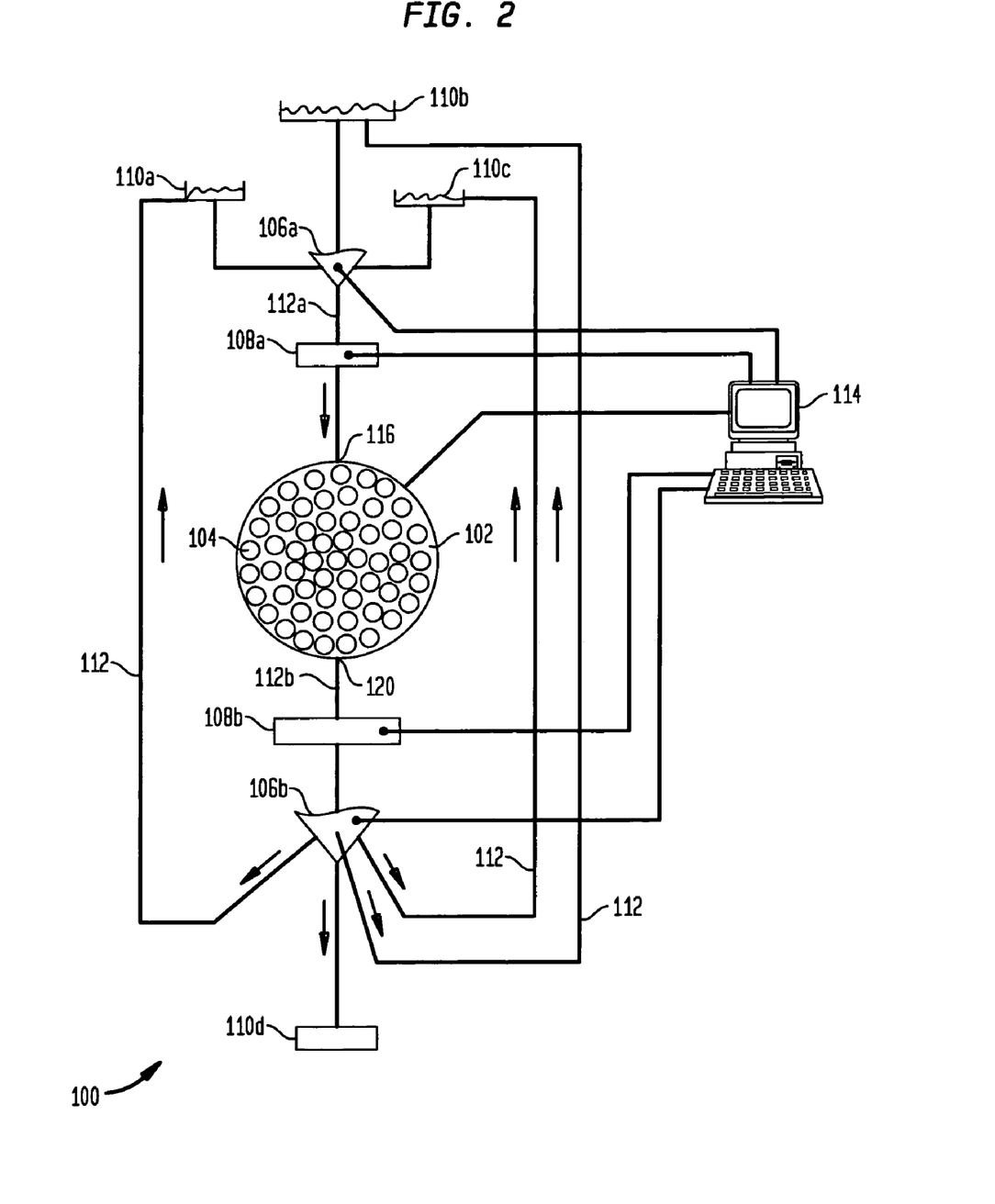
FIG. 2 is a schematic illustration of a flow drive for a dynamic phantom according to the invention.

Referring now to FIG. 2, which illustrates an example of a flow drive 100 for a dynamic phantom according to an example embodiment of the invention, flow drive 100 broadly comprises phantom chamber 102, medium 104, one or more valve assemblies 106, one or more pump assemblies 108, one or more fluid reservoirs 110, conduits 112, and system controller 114.

In the embodiment illustrated in FIG. 2, phantom chamber 102, which is shown as comprising a hollow sphere, is essentially fluid tight, except for inlet 116 and outlet 118, which connect to inlet conduit 112a, and outlet conduit 112b respectively. Phantom chamber 102 is configured for receiving medium 104 therein, which in the illustrated embodiment can comprises Lucite® beads or other granulated-type flowing material for substantially filling the volume of the phantom chamber. Accordingly, phantom chamber 104 can be configured to be openable and sealably closable for purposes of filling the volume thereof with a medium. Phantom chamber 102 and is also illustrated as being communicatively connected to system controller 114, which can comprise a programmable computer and software therefor for controlling/monitoring the phantom. It should be appreciated by those having skill in the art that while phantom chamber 102 is illustrated as comprising a hollow spherical shape, as discussed hereinafter the phantom chamber can comprise a number of shapes and configurations. Similarly, while phantom chamber 102 is preferably formed from Lucite®, or other material having an attenuation substantially equivalent to that of water, materials other than Lucite® can be used, e.g., elastomeric materials.

Figure 3:
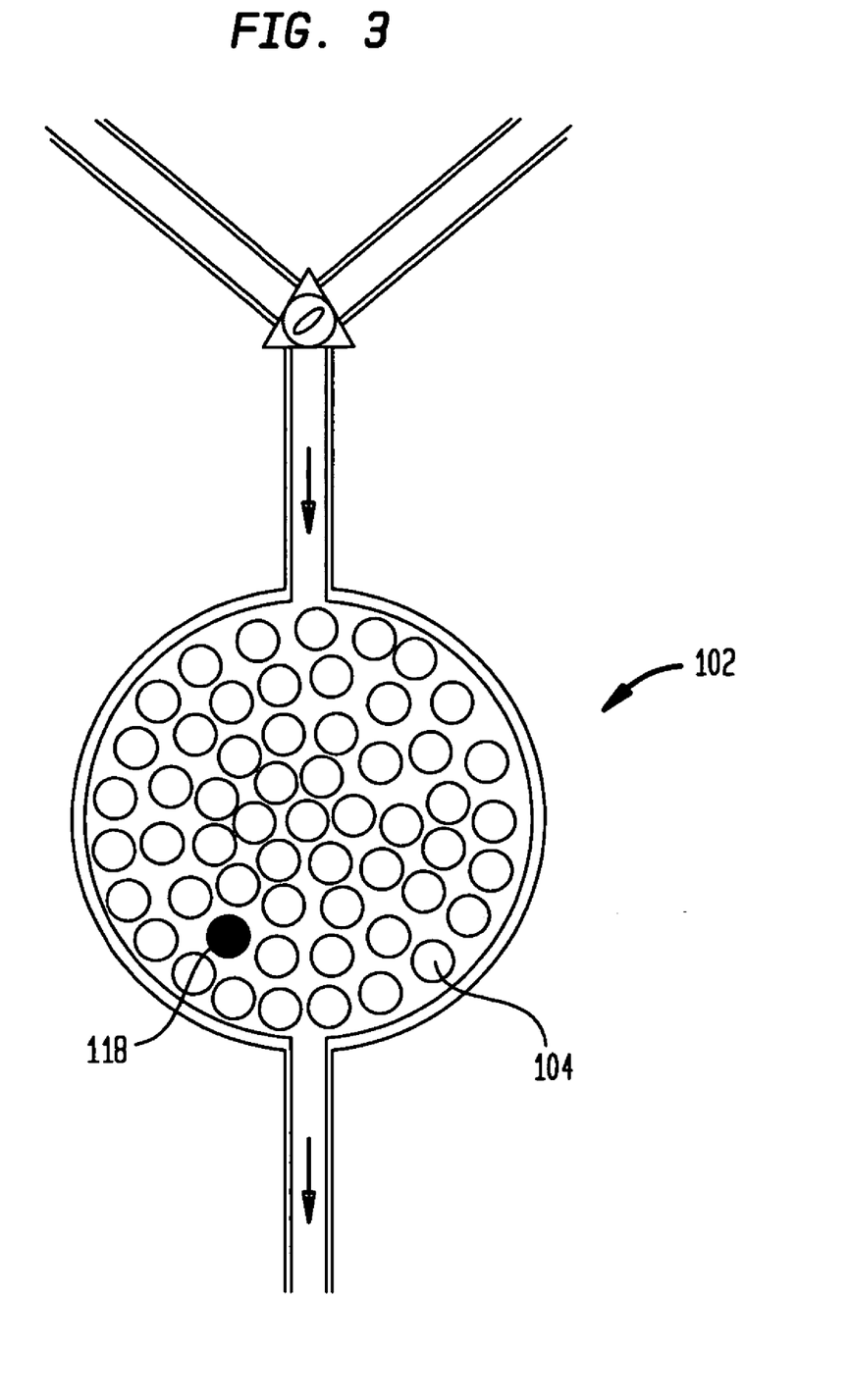
FIG. 3 is a schematic illustration of a phantom according to the invention.

Medium 104 is generally provided for modulating flow through the phantom chamber by creating a tortuous path therethrough, which tends to hinder fluid flow through the chamber to thereby simulate tracer uptake. Medium 104 can further be configured for binding/releasing tracer constituents in, for example, the manner of ion attraction/exchange mechanisms, protein receptor/binder type mechanisms, etc. Depending upon the simulation to be performed, the size of beads and/or granular-type material can range from between <1 mm-10 mm. Additionally, as shown in FIG. 3, medium 104 can be configured to simulate a "diseased" tissue portion, which can comprise a phantom sub-chamber for receiving a different tracer, tracer with a different concentration, or another medium having a different affinity for the tracer being used. In some embodiments, one or more of chamber 102 or medium 104, can be configured to include assemblies such as screen members, to prevent the egress of medium 104 from the chamber. In some embodiments, medium 104 can comprise gels or cellular-type material, e.g. sponge-like material.

Inlet 116 is fluidly connected to inlet conduit 112a and outlet 120 is fluidly connected to outlet conduit 112b. In the illustrated embodiment, inlet conduit 112a can be fluidly connected to one or more fluid reservoirs 110a-c via valve 106a and/or a pump 108a for pumping fluid into the phantom chamber.

Outlet 120 is connected to outlet conduit 112b, which can be connected to valve assembly 106b for directing an outlet fluid to waste reservoir 110d or recycling an outlet fluid back to one of fluid reservoirs 110a, 110b and 110c. In the illustrated embodiment, outlet conduit 112 is fluidly connected to pump 108b for purposes of drawing fluid through the phantom chamber.

Valve assembly 106a is provided for dispensing fluid from one of fluid reservoirs 110a-c into inlet conduit 112a for purposes of being delivered to the phantom chamber by one or more of pumps 108a,b. Alternatively, fluids can be delivered to phantom chamber 102 by manual means, for example, injection thereof with a syringe through a conduit. The advantage, however, of delivering fluids via valves 106 and pumps 108a,b is that each of valve 106a,b and pumps 108a,b can be controlled by system controller 114 to dispense/deliver fluids 110a-c as may be desired and from a remote location. Similarly, valve 106b is provided for directing fluid having passed through the phantom chamber to one of waste reservoir 110d or back to one of reservoirs 110a-c. Valve 106b can also be controlled via controller system 114.

Reservoirs 110a-d are provided for storing fluid for delivery to the phantom chamber. Generally, one each of fluid reservoirs 110a-c can contain one of a neutral fluid (water) (110a), a radiative tracer (110b), and a radiative tracer wash (110c), e.g. Radiac Wash™, for purposes of neutralizing/removing the radiative tracer from the phantom chamber and medium.

System controller 114 is generally provided for directing fluid flow into and out of the phantom chamber 102 and comprises a programmable computer and software therefor for controlling the opening and closing valves 106a,b and pumps 108b. System controller 114 can also be configured for controlling/monitoring contraction/expansion of a dynamic cardiac phantom of the type disclosed in U.S. Pat. App. Pub. No. 2003/0220718 A1.

Accordingly, flow drive for a dynamic phantom 100 can be used in the following manner for simulating tissue uptake: phantom chamber 102 is filled with medium 104 and connected to inlet 116 and outlet 118, as appropriate, valve 106b and pump 108a,b are then directed to issue a neutral fluid from fluid reservoir 110a into the phantom chamber, which neutral fluid can then be returned to the reservoir 110a, or directed to waste reservoir 110d via valve 108b as directed by system controller 114. Monitoring of the phantom chamber 102 can then begin using a medical imaging device. Valve 106a can then be directed by the system controller to begin issuing tracer from fluid reservoir 110b into the phantom chamber. After passing through the phantom chamber and/or binding with medium, the used up tracer can then be returned to fluid reservoir 110b or directed to waste reservoir 110d. Monitoring of the phantom chamber by the medical imaging device is continued for a desired time period to observe wash-in of the tracer. At the end of wash-in, valve 106a can then be directed to issue a radiative tracer wash in fluid reservoir 110c into the phantom chamber. The phantom chamber can then be monitored using the medical imaging device. After passing through the phantom chamber, the radiative wash can be returned to reservoir 110c or directed to waste reservoir 110d by means of valve 108b.

Referring now to FIGS. 3-7a,b, the flow drive for a dynamic phantom 100 can be configured for use with various types of phantom chamber and/or medium. As illustrated in FIG. 3, medium 104 can comprise sub-medium 118, which has a different affinity for a tracer and/or, in the case of a radiative tracer, a radiation level different from medium 104, for purposes of representing or simulating abnormal tissue.

Figure 4:
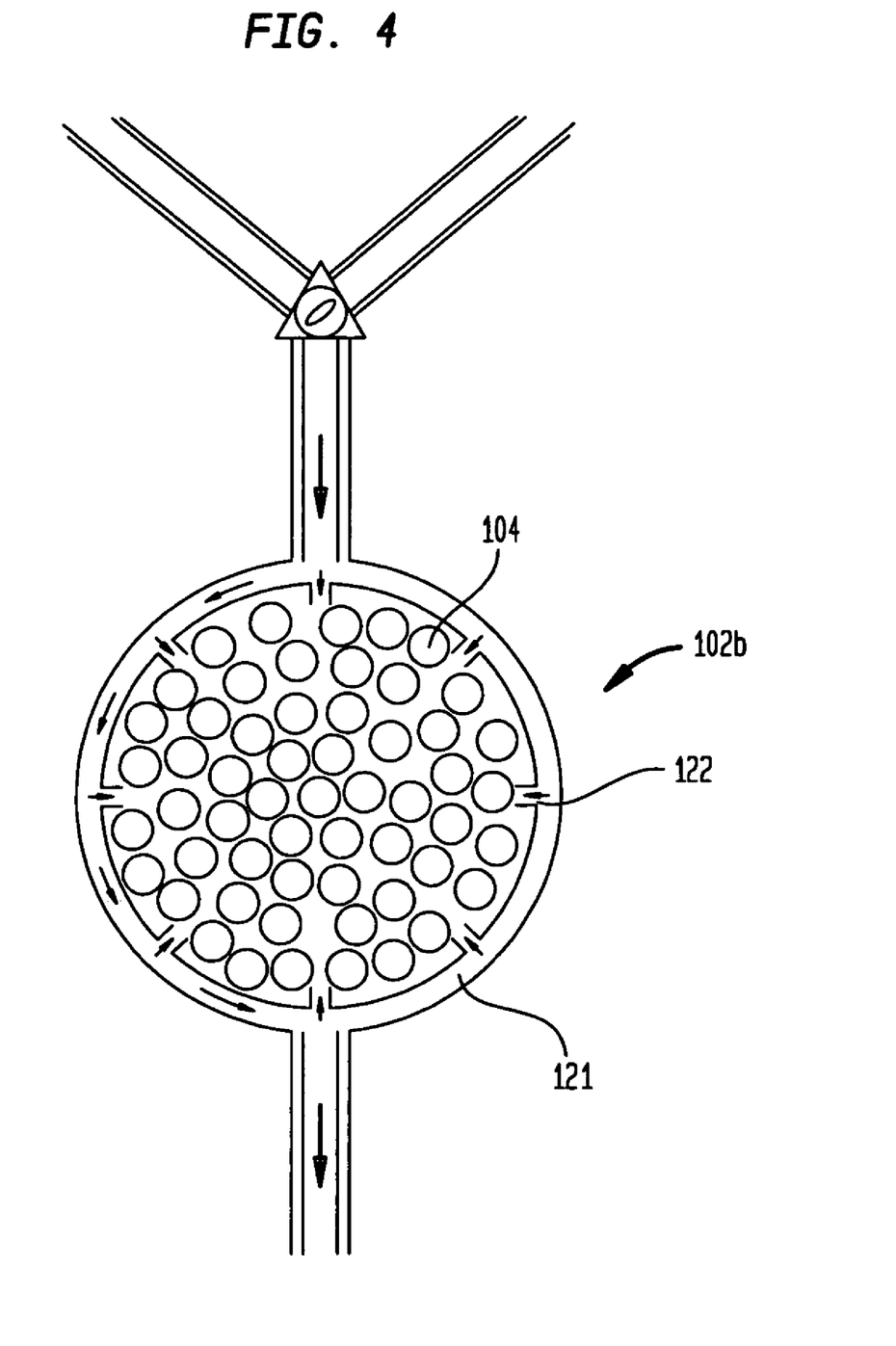
FIG. 4 is a schematic illustration of a phantom according to the invention.

As illustrated in FIG. 4, phantom chamber 102b is illustrated as comprising chamber conduit 121 including a plurality of apertures 122 for uniformly distributing a fluid into the medium.

Figure 5:
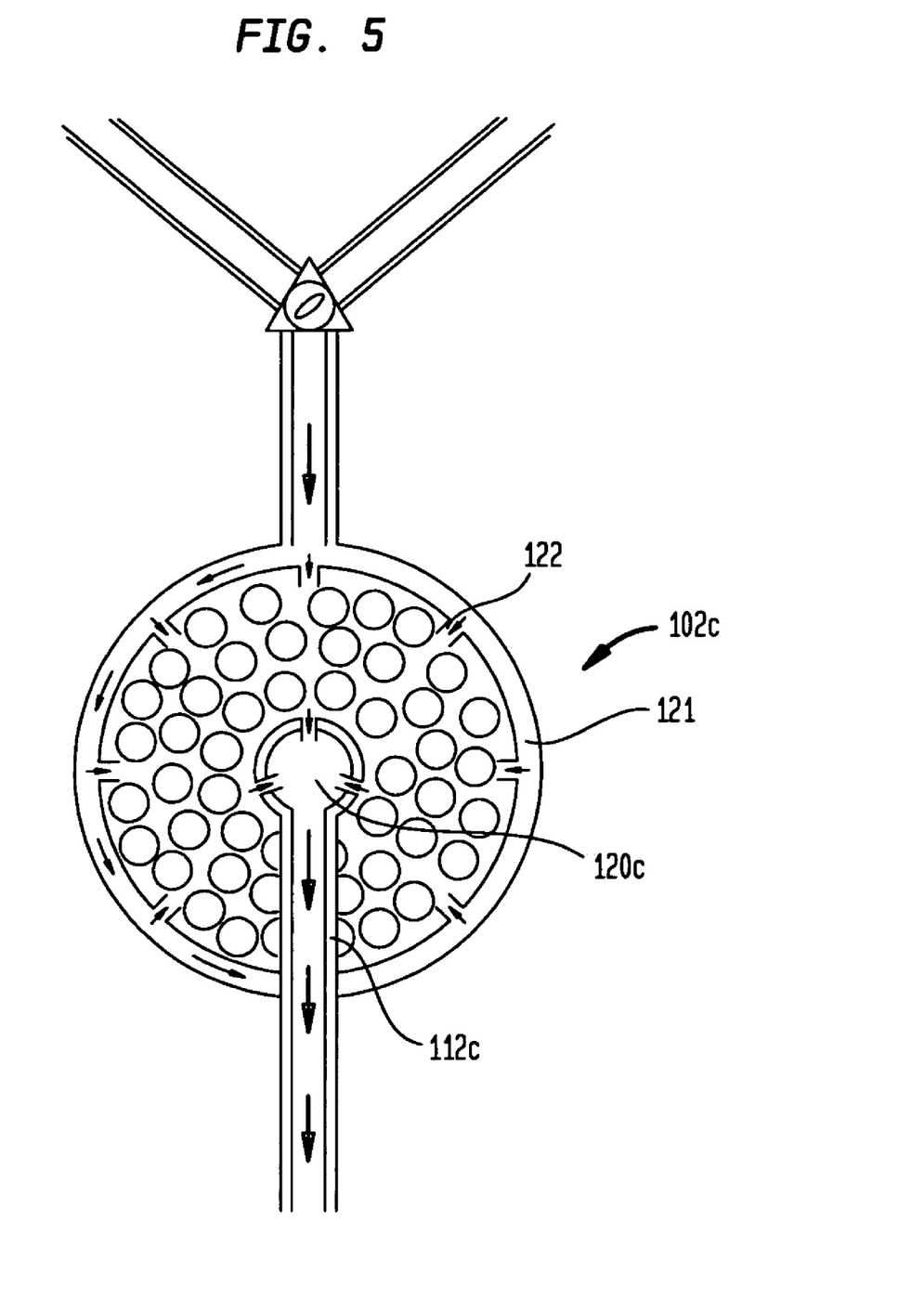
FIG. 5 is a schematic illustration of another phantom according to the invention.

As shown in FIG. 5, phantom chamber 102c is illustrated as comprising chamber conduit 121 including a plurality of apertures 122 for uniformly distributing a fluid into the medium as well as outlet conduit 112c and outlet portion 120c including a plurality of apertures disposed within a portion of the medium.

Figure 6:
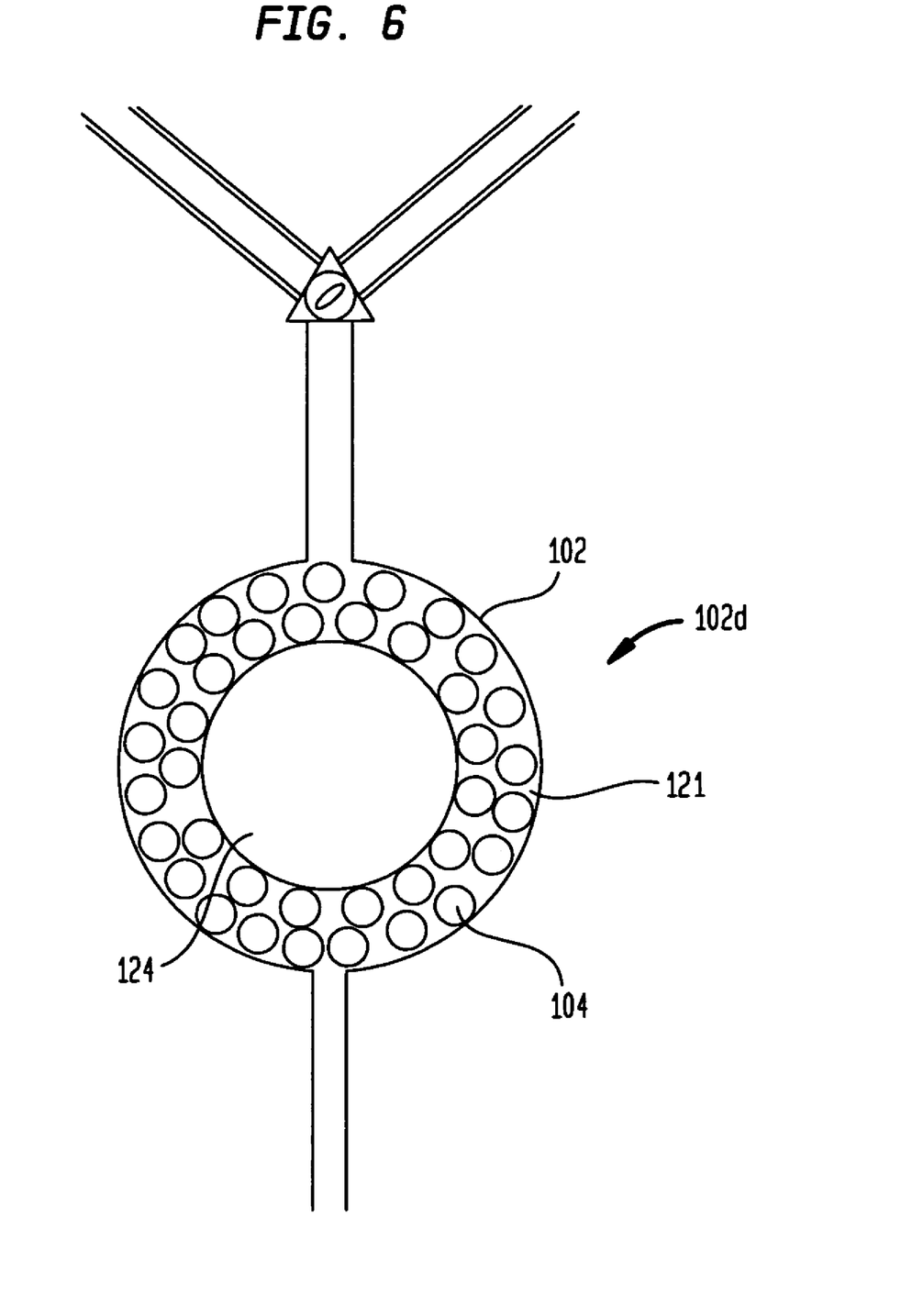
FIG. 6 is a schematic illustration of a dynamic cardiac phantom according to the invention; and, FIG. 7a and 7b are schematic illustrations of the dynamic phantom of FIG. 5 in collapsed and expanded configurations, respectively.
Figure 7A:
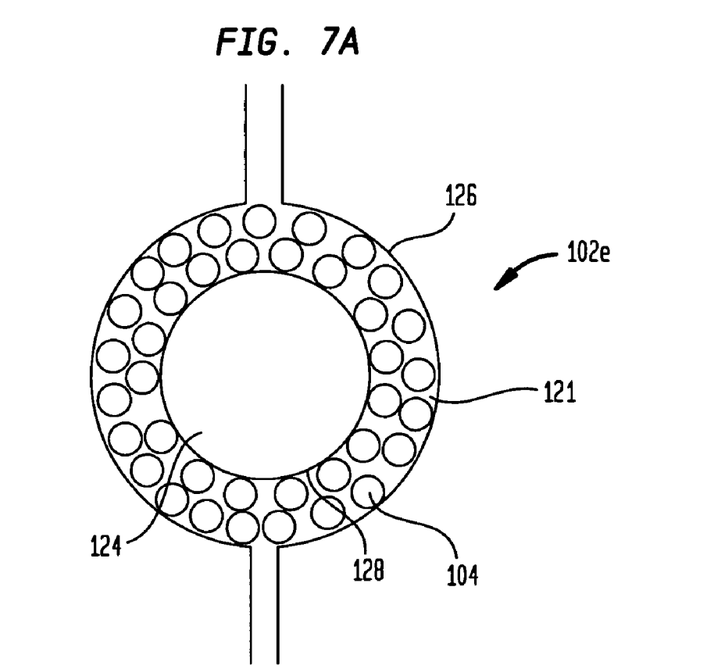
Figure 7B:
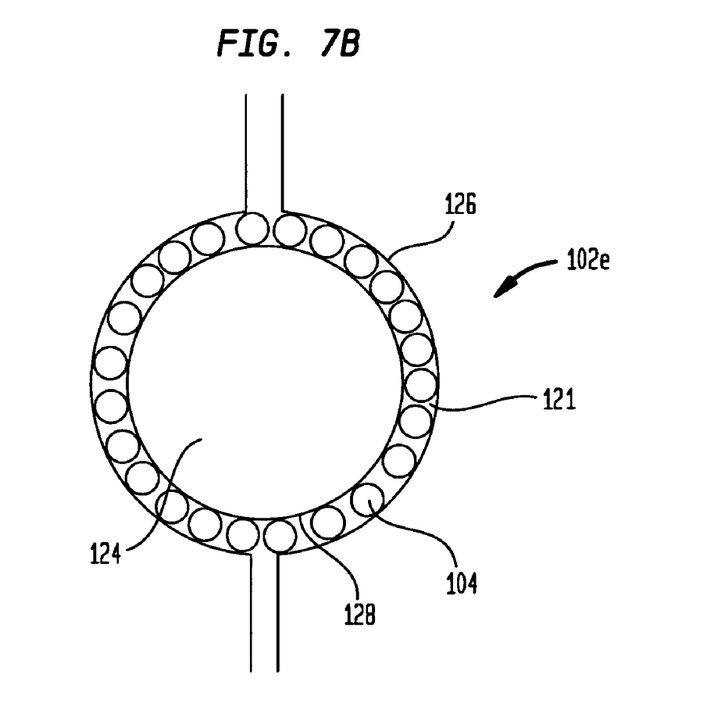

As shown in FIG. 6, phantom chamber 102d is illustrated as comprising core area 124 (which can be solid or hollow) which thereby forms chamber conduit 121. Medium 104 can be disposed within the conduit chamber, e.g., to simulate the myocardium of the human heart. Finally, as shown in FIGS. 7A and 7B, phantom chamber 102e is illustrated as being configured for simulating systolic and diastolic functions of the heart. In this embodiment, phantom chamber 102e comprises first, outer elastomeric sleeve 126 and a second, inner elastomeric sleeve 128, which both surround hollow core area 124. First outer elastomeric sleeve 126 and second inner elastomeric sleeve 128 are separated from one another to form chamber conduit 121 whose volume can be filled with medium 104 for purposes of simulating the myocardium of the human heart. A pump can be used to pump a fluid into/out of hollow core area 124 to cause the inner and outer elastomeric sleeves to expand/contract as may be desired to mimic the beating of a heart. Action of the mechanism used to expand/contract the hollow core can be controlled via the system controller.

Thus, it is seen that an improved flow drive for a dynamic phantom is provided by the present invention, which thereby allows tracer wash-in and washout to be more precisely simulated.

What is claimed is:

1. Apparatus for simulating tracer interaction with a tissue, comprising:
   a chamber for receiving a fluid therein;
   an inlet conduit for conducting said fluid into said chamber;
   an outlet conduit for conducting said fluid out of said chamber;
   a medium disposed within said chamber, said medium configured for modulating fluid flow within said chamber; and,
   a valve assembly for conducting said fluid into said inlet conduit,
   wherein said chamber includes an inner chamber wall and an outer chamber wall, said inner chamber wall and said outer chamber wall disposed relative to one another to thereby form a chamber conduit therebetween, said chamber conduit is fluidly connected to said inlet conduit and said outlet conduit.

2. The apparatus of claim 1 wherein said fluid comprises a radiative tracer.

3. The apparatus of claim 2 wherein said medium is capable of binding said radiative tracer.

4. The apparatus of claim 2 wherein a radiative washout fluid is capable of releasing said radiative tracer bound to said medium.

5. The apparatus of claim 1 wherein said fluid comprises a radiative washout fluid.

6. The apparatus of claim 1 wherein said medium is configured to mimic a tissue.

7. The apparatus of claim 6 wherein said medium mimics at least one of normal tissue and diseased tissue.

8. The apparatus of claim 1 wherein said medium comprises an aggregate-type material.

9. The apparatus of claim 8 wherein said aggregate-type material comprises beads.

10. The apparatus of claim 9 wherein said beads comprise Lucite®.

11. The apparatus of claim 1 wherein said chamber includes a distribution assembly for uniformly distributing an inlet fluid into said chamber.

12. The apparatus of claim 1 wherein said inner chamber wall includes a plurality of apertures for conducting said fluid to said medium.

13. The apparatus of claim 1 wherein said medium is disposed in said chamber conduit.

14. The apparatus of 1 wherein said medium is disposed inward of said inner chamber wall.

15. The apparatus of claim 1 wherein said chamber comprises an expandable chamber wall.

16. A method for simulating tracer interaction with a tissue using a phantom comprising the steps of:
   issuing a first fluid into a chamber comprising a medium via a valve connected to an input conduit;

bathing said medium with said first fluid and allowing said first fluid to exit said chamber via an outlet conduit;

issuing a second fluid into said chamber via said input conduit;

bathing said medium with said second fluid and allowing said second fluid to exit said chamber; and, monitoring said chamber with a medical imaging device when said first fluid and said second fluid is introduced into said chamber, wherein said chamber comprises inner and outer chamber walls thereby forming a chamber conduit, wherein said medium is disposed within said chamber conduit, wherein said chamber conduit is fluidly connected to said inlet conduit and outlet conduit.

17. The method of claim 16, wherein said medium has an attenuation characteristic substantially similar to water.

18. The method of claim 16, wherein said medium comprises an aggregate-type material.

19. The method of claim 18, wherein said medium comprises Lucite beads.

20. The method of claim 16, wherein said first fluid includes a radiative constituent.

21. The method of claim 16, wherein said second fluid includes a radiative washout constituent.

22. The method of claim 16. wherein said medium is disposed within said chamber.

23. The method of claim 16, wherein said chamber comprises an expandable chamber wall.

24. The method of claim 16, wherein said medium is configured to modulate flow of said first and second fluid in said chamber.

25. The method of claim 24, wherein said medium is configured for binding a constituent of said first fluid.

26. The method of claim 25, wherein said constituent comprises a radiative component.

27. The method of claim 25, wherein said second fluid is configured for releasing said constituent from said medium.

* * * * *